United States Patent [19]

Orth et al.

[11] Patent Number: 4,546,190

[45] Date of Patent: Oct. 8, 1985

[54] METHOD FOR PRODUCING 3,5,6-TRICHLORO-1H-PYRIDINE-2-ON

[75] Inventors: Winfried Orth, Hassloch; Werner Fickert, Mannheim, both of Fed. Rep. of Germany

[73] Assignee: Rütgerswerke Aktiengesellschaft, Frankfurt, Fed. Rep. of Germany

[21] Appl. No.: 583,910

[22] Filed: Feb. 27, 1984

[30] Foreign Application Priority Data

Mar. 12, 1983 [DE] Fed. Rep. of Germany ....... 3308800

[51] Int. Cl.$^4$ .......................................... C07D 213/50
[52] U.S. Cl. ..................................... 546/303; 546/345
[58] Field of Search .............................. 546/303, 345

[56] References Cited

U.S. PATENT DOCUMENTS 2,951,844  9/1960  Shermer .............................. 546/345
3,357,984  12/1967  Smith ................................. 546/345
3,682,938  8/1972  Troxel et al. ................... 546/345 X

FOREIGN PATENT DOCUMENTS 2049666  12/1980  United Kingdom ................ 546/303

Primary Examiner—Joseph Paul Brust
Attorney, Agent, or Firm—Beveridge, DeGrandi & Weilacher

[57] ABSTRACT

The compound 3,5,6-trichloro-1H-pyridine-2-on can be produced in technical quantities by passing chlorine gas into the gas space above a solution of 6-chloro-1H-pyridine-2-on in an aqueous carboxylic acid solution and maintaining the reaction temperature between 15° and 30° C. This method permits the production of 3,5,6-trichloro-1H-pyridine-2-on in a one-step process from 2-chloro-6-methoxypyridine.

5 Claims, No Drawings

METHOD FOR PRODUCING 3,5,6-TRICHLORO-1H-PYRIDINE-2-ON

The present invention relates to a new method for producing 3,5,6-trichloro-1H-pyridine-2-on. This compound is an important intermediate product in the synthesis of insecticides.

As synthesis possibilities for this compound, it is common practice to chlorinate 6-bromo-2-ethoxypyridine and subsequently to cleave and halogenate the 6-bromo-3,5-dichloro-2-ethyoxypyridine as well as to chlorinate 6-chloro-1H-pyridine-2-on (den Hertog, De Bruyn; Recueil 70 (1951), 182-190). Both chlorinating reactions occur with aqueous hydrogen peroxide and aqueous hydrochloric acid. As described, they can best be carried out with success in small laboratory batches using, at most, gram quantities. Larger quantities result in uncontrollable side reactions which drastically reduce the yield of the desired product. A cost-effective, semi-technical preparation of 3,5,6-trichloro-1H-pyridine-2-on is not feasible with these methods.

Direct synthesis from trichloroacetylchloride and acetonitrile is known and described in European Patent 00 30 214 A. Apart from the fact that this reaction takes place with highly toxic initial products in a complex pressure reaction, it produces the desired 3,5,6-trichloro-1H-pyridine-2-on as well as 2,3,5,6-tetrachloropyridine, so that a great effort is required to separate these two substances from one another.

Therefore, the primary object of the invention is to provide a method for producing 3,5,6-trichloro-1H-pyridine-2-on in which this compound can be produced economically from a readily available initial substance in the simplest process steps possible, even in large technical batches, with a good yield and purity.

The solution to the problem is provided by the method comprising dissolving 6-chloro-1H-pyridine-2-on in an aqueous carboxlyic acid solution of a carboxylic acid which at the reaction temperature is liquid and inert to chlorine gas and chlorinating in a reaction vessel by passing chlorine gas into the space located above the solution, the reaction temperature being maintained between 15° and 30° C. by cooling. Preferably, the reaction temperature is maintained between 20° and 35° C. It is further preferable to maintain a pressure of between 50 and 200 mbar in the reaction zone. In accordance with a preferred aspect of the invention, the chlorination takes place directly after the ether cleavage of 2-chloro-6-methoxypyridine without isolating the 6-chloro-1H-pyridine-2-on. More particularly, it is preferred to add carboxylic acid to the still hot reaction mixture after the ether cleavage.

The simplest and most economical way to prepare 3,5,6-trichloro-1H-pyridine-2-on is the direct reaction of the readily available 6-chloro-1H-pyridine-2-on with chlorine. Unfortunately, this has not met with success in the past, so that even den Hertog and de Bruyn have followed the method of the indirect chlorination with hydrogen peroxide and hydrogen chloride.

When chlorine gas is passed into a solution of 6-chloro-1H-pyridine-2-on, an extremely exothermic reaction takes place which results in uncontrolled decomposition reactions. These unwanted reactions cannot be suppressed even by permitting the reactants to react only in a moderately concentrated form, e.g., by passing chlorine that has been diluted with a carrier gas into a diluted solution of 6-chloro-1H-pyridine-2-on.

A surprising finding was that the mild and selective chlorination of 6-chloro-1H-pyridine-2-on to form 3,5,6-trichloro-1H-pyridine-2-on succeeded upon passing chlorine gas into a solution of 6-chloro-1H-pyridine-2-on in an aqueous carboxylic acid solution and keeping the temperature between 15° and 30°. The quantity of chlorine absorbed from the gas space by the solution and the chlorine distribution enabled mild, yet cost-effective, completion of the desired chlorinating reaction.

The initial product for the reaction can be pure or technical grade 6-chloro-1H-pyridine-2-on. In another simplified method of carrying out the process of the invention, the reaction mixture resulting from the preparation of 6-chloro-1H-pyridine-2-on from the readily available 2-chloro-5-methoxy-pyridine is obtained directly without previous isolation of the reaction product. To this end, a suspension of 2-chloro-6-methoxypyridine is heated to 100° C. and reacted in portions with approximately twice the molar quantity of concentrated hydrochloric acid and the reaction mixture is distilled to reflux. This addition of acid takes approximately 2-4 hours and is followed by a 15-20 hour secondary reaction at the boiling temperature of the mixture. During this ether cleavage reaction methyl chloride is released, which is collected in pure form and can be used for other syntheses. The remaining reaction mixture serves as initial product for the chlorinating reaction. It is reacted in the hot state with a liquid carboxylic acid or an aqueous carboxylic acid solution and cooled to 15°-30° C.

If pure 6-chloro-1H-pyridine-2-on is used as the initial product for the chlorinating reaction, it is dissolved in an aqueous, approximately 30-70%, carboxylic acid solution. The quantity of carboxylic acid should be sufficient to keep the 6-chloro-1H-pyridine-2-on in solution at the reaction temperature.

Carboxylic acids that are inert to chlorine at the reaction temperature, i.e. between 15° and 30° C. and which are liquid at this temperature are well suited, e.g., acetic acid, propionic acid, butyric acid or valeric acid, but also those that are substituted or branched in the alkyl residue such as, for example, methoxy-acetic, dimethylacetic, methylacetic or ivaleric acid. Generally, the acids are aliphatic monocarboxylic acids containing from 2 to 6 carbons.

The chlorinating reaction occurs in a closed vessel which is provided with an agitator and with at least two closable openings through which gas can be passed, and if necessary, discharged into the gas space above the solution. The reaction vessel should also permit easy sampling. The solution is stirred while being cooled and chlorine gas is passed into the vessel and over the solution, with the gas space preferably being subjected to a light overpressure of approximately 50-200 mbar. The addition of chlorine must be measured in such a way that the reaction temperature does not exceed the prescribed range. This requires approximately 5-10 hours.

The 3,5,6-trichloro-1H-pyridine-2-on obtained as a result of this reaction precipitates during the reaction, forming a suspension.

When the reaction is completed, the excess chlorine gas is removed by adding a small quantity of sodium sulfite. This results in better color stability of the end product which is then filtered off, washed and dried.

The following example is illustrative of the invention, but is not intended to be limiting.

EXAMPLE

Into a 10-liter 3-neck flask containing a vigorously stirred mixture consisting of 861 g (6 mole) 2-chloro-6-methoxypyridine and 100 ml water, there is dropped at regular intervals for over a period of 2.5 hours, 1167 g (12 mole) chemically pure, concentrated hydrochloric acid. This is followed by a 16-hour secondary reaction at reflux temperature. Thereafter, 5000 ml is added to a 60% acetic acid solution, whereupon under a slight overpressure (100 mbar) 980 g chlorine gas is passed into the gas space above the solution for 7 hours, during which the temperature of the reaction mixture is maintained at 20°–2° C. through cooling. When the chlorine addition is completed, 20 g sodium hydrogen sulfite is added. The suspension is stirred for 15 more minutes. Then, 1120 g 50% soda lye is dropped in at 20°–30° C., whereupon the product is siphoned off and washed with water until the filtrate reacts neutral. The end product, which is dried at 100° C., has a melting point of 175° C. (Lit. 174°–175° C.), yield 1100 g=93% of the theoretically expected value.

Further modifications and variations of the invention will be apparent to those skilled in the art from the foregoing and are intended to be encompassed by the claims appended hereto.

We claim:

1. A method for producing 3,5,6-trichloro-1H-pyridine-2-on comprising dissolving 6-chloro-1H-pyridine-2-on in an aqueous carboxylic acid solution which, at the reaction temperature, is liquid and inert to chlorine gas and chlorinating in a reaction vessel by passing chlorine gas into a space located above said solution but not into the solution, said reaction temperature being maintained between 15° and 30° C. through cooling.

2. The method as set forth in claim 1, further comprising maintaining the temperature between 20° and 25° C.

3. The method as set forth in claim 1, further comprising maintaining a light overpressure between 50 and 200 mbar in the gas space.

4. A method for producing 3,5,6-trichloro-1H-pyridine-2-on comprising heating a suspension of 2-chloro-6-methoxypyridine and reacting with concentrated hydrochloric acid, distilling at reflux to bring about cleavage of the resulting ether, thereafter adding aqueous carboxylic acid which at the reaction temperature is liquid and inert to chlorine gas and chlorinating in a reaction vessel by passing chlorine gas into a space located above said solution but not into the solution, said reaction temperature being maintained between 15° and 30° C. through cooling.

5. The method as set forth in claim 4, after said ether cleavage said carboxylic acid is added to said still-hot reaction mixture.

* * * * *